United States Patent
Zakaria et al.

(10) Patent No.: US 11,390,799 B2
(45) Date of Patent: Jul. 19, 2022

(54) AQUEOUS DELAYED ACID SYSTEM FOR WELL STIMULATION

(71) Applicant: Baker Hughes Holdings LLC, Houston, TX (US)

(72) Inventors: Ahmed S. Zakaria, Houston, TX (US); Sumit Bhaduri, The Woodlands, TX (US); Frances H. DeBenedictis, Spring, TX (US); Paul S. Carman, Spriing, TX (US)

(73) Assignee: Baker Hughes Holdings LLC, Houston, TX (US)

( * ) Notice: Subject to any disclaimer, the term of this patent is extended or adjusted under 35 U.S.C. 154(b) by 0 days.

(21) Appl. No.: 16/900,000

(22) Filed: Jun. 12, 2020

(65) Prior Publication Data

US 2020/0399530 A1   Dec. 24, 2020

Related U.S. Application Data

(60) Provisional application No. 62/865,095, filed on Jun. 21, 2019.

(51) Int. Cl.
*C09K 8/74*   (2006.01)
*C07C 215/40*   (2006.01)
(Continued)

(52) U.S. Cl.
CPC ............... *C09K 8/74* (2013.01); *C07C 215/40* (2013.01); *C07F 9/062* (2013.01); *C09K 8/604* (2013.01); *C09K 8/68* (2013.01); *C09K 8/885* (2013.01)

(58) Field of Classification Search
CPC . C09K 8/74; C09K 8/604; C09K 8/68; C09K 8/885; C07C 215/40; E21B 43/26; E21B 43/16
See application file for complete search history.

(56) References Cited

U.S. PATENT DOCUMENTS 4,466,893 A   8/1984 Dill
6,572,789 B1   6/2003 Yang et al.
(Continued)

FOREIGN PATENT DOCUMENTS

| GB | 2304754 A | 3/1997 |
| WO | 2014004697 A2 | 1/2014 |
| WO | 2017040553 A1 | 3/2017 |

OTHER PUBLICATIONS

U.S. Appl. No. 17/065,758, filed Oct. 8, 2020 (application and drawings).
(Continued)

*Primary Examiner* — Silvana C Runyan
(74) *Attorney, Agent, or Firm* — John Wilson Jones; Jones Delflache LLP

(57) ABSTRACT

The disclosure relates to an aqueous acidizing fluid. In addition to an acid, the fluid contains an organophosphorus surfactant and/or an acid retarder. The organophosphorus surfactant may be an amino phosphonate or a phosphino carboxylate. The acid retarder comprises the combination of urea or a urea derivative and a bifunctional organic compound. Suitable bifunctional organic compounds contain at least one quaternary ammonium or phosphonium and at least one alcohol as well as salts of nitrogen containing heterocyclic rings.

19 Claims, 7 Drawing Sheets

(51) Int. Cl.
*C07F 9/06* (2006.01)
*C09K 8/60* (2006.01)
*C09K 8/68* (2006.01)
*C09K 8/88* (2006.01)

(56) References Cited

U.S. PATENT DOCUMENTS

| | | | |
|---|---|---|---|
| 6,737,386 B1 | 5/2004 | Moorhouse et al. | |
| 6,794,524 B1 | 9/2004 | Imperante et al. | |
| 7,094,738 B2 | 8/2006 | Patel et al. | |
| 2005/0054540 A1* | 3/2005 | Patel | C09K 8/06 |
| | | | 507/128 |
| 2005/0124738 A1 | 6/2005 | Sivik et al. | |
| 2005/0126786 A1* | 6/2005 | Fu | C09K 8/74 |
| | | | 166/307 |
| 2006/0131022 A1 | 6/2006 | Rae et al. | |
| 2008/0004187 A1 | 1/2008 | Pena et al. | |
| 2008/0234147 A1 | 9/2008 | Li et al. | |
| 2011/0130312 A1* | 6/2011 | Notte | C09K 8/602 |
| | | | 507/236 |
| 2015/0013984 A1 | 1/2015 | Abivin et al. | |
| 2015/0344771 A1 | 12/2015 | Jiang et al. | |
| 2016/0177170 A1* | 6/2016 | Janak | C09K 8/74 |
| | | | 507/242 |
| 2016/0288045 A1 | 10/2016 | Kramer et al. | |
| 2016/0298024 A1 | 10/2016 | Panga et al. | |
| 2018/0244982 A1 | 8/2018 | Yakovlev et al. | |
| 2018/0265808 A1 | 9/2018 | Gross | |
| 2018/0305601 A1 | 10/2018 | Champagne et al. | |
| 2018/0346798 A1* | 12/2018 | Abdel-Fattah | E21B 43/16 |
| 2019/0382649 A1* | 12/2019 | Jiang | C09K 8/72 |

OTHER PUBLICATIONS

International Search Report and Written Opinion for PCT/US2020/037453 dated Sep. 16, 2020 in corresponding application.

\* cited by examiner

AQUEOUS DELAYED ACID SYSTEM FOR WELL STIMULATION

This application claims the benefit of U.S. patent application Ser. No. 62/865,095, filed on Jun. 21, 2019, herein incorporated by reference.

FIELD

The disclosure relates to an aqueous delayed acid system and methods of using the same. In addition to containing an acid, the system contains an acid retarder and/or an organophosphorus surfactant of an amino phosphonate or a phosphino carboxylate; the acid retarder may comprise the combination of urea or a urea derivative and at least one bifunctional organic compound containing both at least one quaternary phosphonium or ammonium moiety and at least one hydroxyl group. The bifunctional organic compound may further be a salt of a nitrogen containing heterocyclic ring.

BACKGROUND

Subterranean formations penetrated by an oil or gas well are often stimulated to enhance the flow of hydrocarbons to the wellbore. Acidizing is a common stimulation procedure where aqueous acidic solutions are used to open channels around the wellbore, thereby increasing permeability of the formation and improving hydrocarbon flow rate. The use of acidizing is often preferred in the treatment of carbonate formations since the reaction products are soluble in the spent acid. In addition to enhancing the production of hydrocarbons, blockages caused by natural or man-made conditions may further be removed during acid stimulation. For instance, formation damage caused by drilling mud invasion and clay migration may be removed during the process.

The two principal acidizing methods are acid fracturing and matrix stimulation. In each of these methods, the acidizing fluid is a low pH acid or an acid-forming material. Rapid reaction (or spending) of the acid during acidizing is attributable to a lack of restriction to the mobility of protons.

In acid fracturing, acidizing fluid is pumped into the well at a pressure sufficient to create or enhance fractures. Fracture faces are then etched with the acid and the acid is allowed to react with the surrounding formation to create conductive channels. Penetration of the acid deep into the formation is difficult in acid fracturing if the acid reacts too quickly.

In matrix acidizing, often used to enhance near-wellbore permeability, the acidizing fluid is injected into the formation at pressures lower than those which induce fracturing. The acid or acid-forming material reacts with minerals in the formation and forms conductive highly branched flow channels or wormholes, thereby creating flow channels from the formation to the wellbore. As subsequent fluid is pumped into the formation, it tends to flow along the channel, leaving the rest of the formation untreated. The successful creation of wormholes is made difficult if the acid reacts too quickly and dissolves the carbonate or formation matrix.

Radial penetration, also caused by the quick reaction of the acid with the wellbore coating upon introduction into the formation, also presents a severe limitation in acidizing operations. Further, rapid reaction of the acid causes severe corrosion to pumping and wellbore tubing.

Common methods for retarding the acid reaction include suspending the acid in a water-in-oil emulsion as well as the use of gellants. Such methods are often ineffective. More effective methods of retarding the acid reaction with the formation have therefore been sought.

SUMMARY

In an embodiment, the disclosure relates to an aqueous delayed acid system containing an acid. In addition to the acid, the aqueous delayed acid system contains an organophosphorus surfactant and/or an acid retarder. The organophosphorus surfactant may be an amino phosphonate or a phosphino carboxylate. The acid retarder comprises the combination of urea or a urea derivative and a bifunctional organic compound. Suitable bifunctional organic compounds include those containing both a quaternary phosphonium or ammonium moiety and an alkanol. Other bifunctional organic compounds may be a salt of a nitrogen containing heterocyclic ring.

In an embodiment, the aqueous delayed acid system recited above is used in acid fracturing wherein the system may be pumped into the well under pressure to create or enhance fractures. The fracture faces are then etched with the acid system and the acid reacts with the surrounding formation to create conductive channels. In another embodiment, the aqueous delayed acid system recited above is used in matrix acidizing. The creation and penetration of wormholes may be enhanced by retarding or slowing down the spending of the acid in the formation.

In another embodiment, a method of acidizing a subterranean formation is provided wherein the formation is contacted with an aqueous delayed acid system. The aqueous delayed acid system contains, in addition to an acid, an organophosphorus surfactant and/or an acid retarder. The organophosphorus surfactant may be an amino phosphonate or a phosphino carboxylate. The acid retarder comprises the combination of urea or a urea derivative and a bifunctional organic compound. Suitable bifunctional organic compounds include those having both a quaternary phosphonium or ammonium moiety and an alkanol of at least one —OH group. Other suitable bifunctional organic compounds include salts of a nitrogen containing heterocyclic ring.

In an embodiment, a method of acidizing using an aqueous delayed acid system is provided wherein the aqueous delayed acid system contains an acid and an organophosphorus surfactant wherein spending of the acid of the aqueous delayed acid system is retarded in the formation by adsorbing onto the surface of the formation the organophosphorus surfactant. The organophosphorus surfactant limits sites for bonding of the acid onto the formation surface. The organophosphorus surfactant may include an amino phosphonate or a phosphino carboxylate.

In an embodiment, a method of acidizing using an aqueous delayed acid system as provided above is provided wherein the aqueous delayed acid system contains an acid and an acid retarder and wherein spending of the acid of the aqueous delayed acid system is retarded in the formation by disrupting hydrogen bonding of the water (or brine) of the treatment fluid, thereby limiting the rate of dissociation of the acid and the diffusion of protons to the surface of the formation. The acid retarder may comprise the combination of urea or a urea derivative and a bifunctional organic compound. Suitable bifunctional organic compounds are those containing both a quaternary phosphonium or ammonium moiety and at least one —OH group. Other suitable bifunctional organic compounds include salts of a nitrogen containing heterocyclic ring.

In another embodiment, a method of acidizing a subterranean carbonate formation is provided wherein an aqueous delayed acid system is introduced into the well. In addition to an acid, the aqueous delayed acid system contains an organophosphorus surfactant and/or an acid retarder. The organophosphorus surfactant may be an amino phosphonate or a phosphino carboxylate. The acid retarder comprises the combination of urea or a urea derivative and a bifunctional organic compound. Suitable bifunctional organic compounds include those which contain both a quaternary phosphonium or ammonium moiety and at least one —OH group. Other suitable bifunctional organic compounds include salts of a nitrogen containing heterocyclic ring.

In still another embodiment, a method of acidizing a subterranean formation penetrated by a well is provided wherein the formation is contacted with an aqueous delayed acid system which contains an acid as a first member and as a second member an organophosphorus surfactant and/or an acid retarder. The organophosphorus surfactant may be an amino phosphonate or a phosphino carboxylate. The acid retarder comprises the combination of urea or a urea derivative and a bifunctional organic compound. The bifunctional organic compound contains both a quaternary phosphonium or ammonium moiety and at least one —OH group. Other suitable bifunctional organic compounds include salts of a nitrogen containing heterocyclic ring. Spending of the acid is delayed with the second member.

In another embodiment, a method of slowing down the reaction with a carbonate matrix during acidizing of the formation is provided. In this embodiment, an aqueous delayed acid system which contains, in addition to an acid, an organophosphorus surfactant and/or acid retarder is introduced into a well penetrating the formation. The organophosphorus surfactant may be an amino phosphonate or a phosphino carboxylate. The acid retarder comprises the combination of urea or a urea derivative and a bifunctional organic compound. Suitable bifunctional organic compounds contain both a quaternary phosphonium or ammonium moiety and at least one —OH group. Other suitable bifunctional organic compounds include a salt of a nitrogen containing heterocyclic ring. When the aqueous delayed acid system contains the organophosphorus surfactant, spending of the acid of the aqueous delayed acid system is retarded in the well by adsorbing onto the surface of the formation the organophosphorus surfactant. This limits sites for bonding of the acid onto the formation surface. When the aqueous delayed acid system contains the acid retarder, spending of the acid of the aqueous delayed acid system is retarded in the well by disrupting hydrogen bonding of the water (or brine) of the treatment fluid. As a result, the rate of acid dissociation and the diffusion of the acid protons to the rock surface of the formation is reduced.

BRIEF DESCRIPTION OF THE DRAWINGS

The following figures are part of the present specification, included to demonstrate certain aspects of various embodiments of this disclosure and referenced in the detailed description herein.

DETAILED DESCRIPTION

Figure 1:
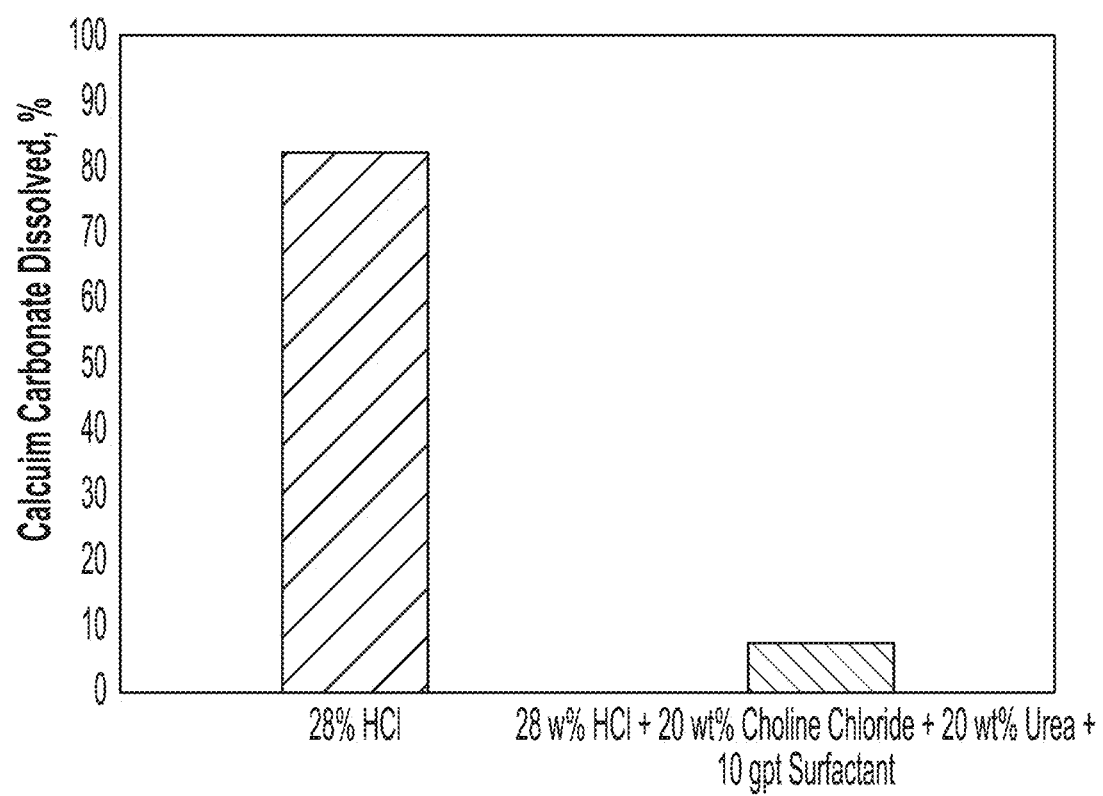
FIG. 1 contrasts calcium carbonate dissolved using an aqueous acidizing solution containing only 28 weight percent HCl with an aqueous acidizing solution containing 28 weight percent HCl, choline chloride, urea, and an amine organophosphorus surfactant.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of exemplary embodiments, is not intended to limit the claims of this patent or any patent or patent application claiming priority hereto. On the contrary, the intention is to cover all modifications, equivalents and alternatives falling within the spirit and scope of the claims. A person of ordinary skill in the art will understand that the embodiments of the disclosure may be practiced without employing all of the specific details and that embodiments of the disclosure may be practiced in conjunction with conventional techniques employed in the industry.

The terms "including" and "comprising" are used herein and in the appended claims in an open-ended fashion, and thus should be interpreted to mean "including, but not limited to . . . ."

Further, reference herein and in the appended claims to components and aspects in a singular tense does not necessarily limit the present disclosure or appended claims to only one such component or aspect, but should be interpreted generally to mean one or more, as may be suitable and desirable in each particular instance The use of the terms "a" and "an" and "the" and similar referents (especially in the context of the following claims) are to be construed to cover both the singular and the plural, unless otherwise indicated herein or clearly contradicted by context.

All ranges disclosed herein are inclusive of the endpoints. A numerical range having a lower endpoint and an upper endpoint shall further encompass any number and any range falling within the lower endpoint and the upper endpoint. For example, every range of values (in the form "from a to b" or "from about a to about b" or "from about a to b," "from approximately a to b," "between about a and about b," and any similar expressions, where "a" and "b" represent numerical values of degree or measurement is to be understood to set forth every number and range encompassed within the broader range of values and inclusive of the endpoints.

The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, reaction products, and the like.

The word "ammonium" shall refer to an organic moiety of quaternary nitrogen, $NR_4^+$, wherein each R is independently a hydrogen, alkyl or a substituted alkyl group provided at least one R is an alkyl or substituted alkyl group.

The word "amino" shall refer to ammonium as well as trivalent nitrogen moieties.

All references are incorporated herein by reference.

The aqueous compositions disclosed herein are useful in retarding acid reactivity. The aqueous delayed acid system described herein is especially useful in acidizing carbonate reservoirs, such as limestone, chalk and dolomite. Further, the aqueous delayed acid system may be used in fracture acidizing of carbonate reservoirs as well as siliceous and other formations.

When the aqueous delayed acid system is used in matrix acidizing, significant control in the creation and penetration of wormholes during acid matrix stimulation is possible.

Further, the aqueous delayed acid system described herein decreases friction pressures during pumping of treatment fluid into the well.

The aqueous delayed acid system need not contain any oil or other components (such as emulsifying agents) since the fluid is not an emulsion. As such, the solvent of the fluid may be just water. The water of the aqueous delayed acid system may be fresh water or brine. The aqueous delayed acid system does not contain a polymer gel or a linear or crosslinked polymer. The aqueous delayed acid system is not an emulsion, i.e., the aqueous delayed acid system is not a water-in-oil emulsion or an oil-in-water emulsion. Use of the aqueous delayed acid system minimizes formation damage.

In an embodiment, the viscosity of the aqueous delayed acid system may be from about 0.5 cP to about 10 cP (measured on a Model 35 Fann viscometer having a RIB1 rotor and bob assembly rotating at 300 rpm at 225° F.).

The amount of water in the aqueous delayed acid system is that amount sufficient to dissolve the acid and the amino organophosphorus surfactant and/or acid retarder. In various embodiments, the amount of water in the aqueous delayed acid system is less than 80 wt %, or less than 60 wt %, or less than 40 weight percent or less than 20 wt %, or even less than 8 wt %.

The aqueous acidizing fluid, in addition to containing an acid, contains an organophosphorus surfactant and/or an acid retarder. The organophosphorus surfactant may be an amino phosphonate or a phosphino carboxylate. The acid retarder comprises the combination of urea or a urea derivative and a bifunctional organic compound. Suitable bifunctional organic compounds include those containing at least one quaternary organophosphonium or ammonium moiety and at least one —OH group. Other suitable bifunctional organic compounds include salts of a nitrogen containing heterocyclic ring.

When used in matrix acidizing, the aqueous delayed acid system delays spending of the acid and thus enhances the creation and penetration of the wormholes. This enhances the permeability of the formation.

When the aqueous delayed acid system contains the organophosphorus surfactant, the organophosphorus surfactant likely adsorb onto the surface of the formation. This inhibits the reactivity of the acid by limiting sites for bonding of the acid onto the formation surface.

When the aqueous delayed acid system contains the acid retarder, it is believed it reduces diffusion of protons to the surface of the rock. Since proton transport to the wormhole wall is slowed down during matrix acidizing, acid retardation increases. Further, the acid protons are less available for reaction as the rate of acid dissociation is reduced.

The acid is typically an inorganic acid such as hydrochloric acid, nitric acid, phosphoric acid, sulfuric acid, hydrofluoric acid, hydrobromic acid, perchloric acid and hydrogen iodide.

Organic acids may also be used. Exemplary organic acids are alkanesulfonic acids (such as methanesulfonic acid), arylsulfonic acids, acetic acid, formic acid, alkyl carboxylic acids, acrylic acid, lactic acid, glycolic acid, malonic acid, fumaric acid, glutamic acid, citric acid, tartaric acid, glutamic acid-N,N-diacetic acid (GLDA), hydroxyl ethylene diameinetriacetic acid (HDEDTA), N-hydroxyethyl-N, N', N'-ethylenediaminetriacetic acid (HEDTA), hydroxyethyl-iminodiacetic acid (HEIDA), diethylenetriaminepentaacetic acid (DTPA) and cyclohexylenediaminetetraacetic acid (CDTA) or an organic diacid mixture of adipic, succinic and glutaric acids available as StimCarb HTOA from Baker Hughes Holdings LLC.

Mixtures of such acids may further be employed. For instance, the acid of the aqueous delayed acid system may contain a mixture of inorganic acids, such as HCl and HF, as well as mixtures of organic acids. Further, the acid of the aqueous delayed acid system may be a mixture of one or more inorganic acids and one or more organic acids.

The amount of acid in the aqueous delayed acid system is up to about 36 wt %, or from about 5 to about 36 wt %, or from about 5 to about 28 wt %, or from about 5 to about 20 wt % (based on the total weight of the aqueous delayed acid system). In a preferred embodiment, the acid is hydrochloric acid of, typically in an amount from 15 to 28 weight percent.

The organophosphorus surfactant of the aqueous delayed acid system preferably has a hydrophilic and hydrophobic tail and include those having at least one —OH group, at least one alkyl group, and at least one ammonium or a phosphonium group Exemplary organophosphorus surfactants are amino phosphonates. Suitable amino phosphonates include phospholipids, such as those of the structure (I):

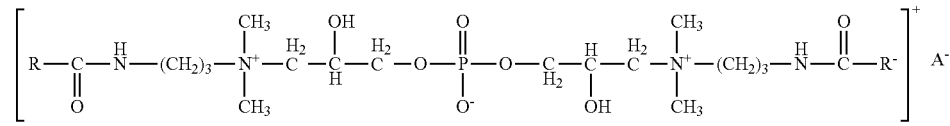

wherein R and R' are $C_6$ to $C_{25}$ hydrocarbon groups and A is any suitable anion to counter the cationic charge, preferably a conjugate base of a strong inorganic acid or organic acid. Preferably, the anion is selected from the group consisting of halides, nitrates, sulfates, phosphates, anions of $C_1$ to $C_{10}$ organic acids, and combinations of these. Preferred phospholipids include one or more fatty acid amidopropyl propylene glycol dimonium phosphate salts in which the fatty acid is a $C_{10}$ to $C_{25}$ fatty acid. These include cocadmidopropyl PG-dimonium chloride phosphate salts (also known as 1-propanaminium 3,3',3"-[phosphinylidynetris(oxy)]tris[N-(3-aminopropyl)-2-hydroxy-N,N-dimethyl-N,N',N"-tri-$C_{6-18}$ acyl derivatives. In another preferred embodiment, the amino organophosphorus surfactant is ricinoleamidopropyl PG-dimonium chloride phosphate. Preferred are dilinoleamidopropyl PG-dimonium chloride phosphates such as sodium cocamidopropyl PG-dimonium chloride phosphate and sodium dilinoleamidopropyl PG-dimonium chloride phosphate.

Other preferred phospholipids include dimer dilinoleamido-propyl PG-dimonium chloride phosphate; linoleamidopropyl PG-dimonium chloride phosphate dilinoleamidopropyl PG-dimonium chloride phosphate as well as mixtures thereof.

Preferred surfactants also include 1-propanaminium, 3,3',3"-[phosphinylidynetris(oxy)]tris[N-(3-aminopropyl)-2-hydroxy-N,N-dimethyl-, N,N',N"-tri-$C_{6-18}$ acyl derivatives trichlorides (CAS 83682-78-4).

In another embodiment, the amino organophosphonate surfactant may be an ester based phosphobetaine having, as an amine group, quaternized nitrogen. Hence the products are amphoteric, having both an anionic and cationic group present on the same pendant group. The compounds may have a pendant amphoteric group, and an ester linkage and may be represented by the formula (II)"

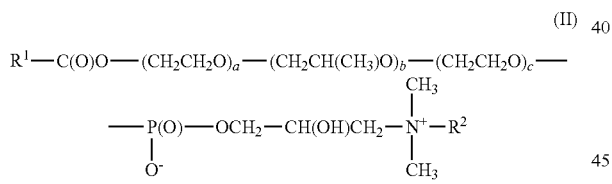

(II)

wherein:
$R^1$ is alkyl or alkylene having between 7 and 21 carbon atoms;
a, b and c independently are integers ranging from 0 to 20, with the proviso that a+b+c be equal to or greater than 1;
$R^2$ is selected from the group consisting of alkyl having 7 to 21 carbon atoms and $R^3$—C(O)—N(H)—(CH$_2$)$_2$— where $R^3$ is alkyl having 7 to 21 carbon atoms.
In an embodiment, b and c are 0 and a is 3. Such compounds may be prepared as set forth in U.S. Pat. No. 6,794,524.

In another embodiment, the amino phosphonate surfactant may be an oil soluble blend of a tertiary alkyl amine and an amino phosphonic acid. The tertiary alkyl is typically a tertiary alkyl primary amine having at least one amine group. The amines typically may contain from about 12 to about 14 carbon atoms. Suitable proportions of tertiary amine:amino phosphonic acid are those having a weight ratio of 100:1 to 1:3, more usually 8:1 to 3:2 for amine to amino phosphonic acid.

Examples of suitable amino phosphonic acids are hexamethylene diamine tetrakis (methylene phosphonic acid); diethylene triamine tetra (methylene phosphonic acid); diethylene triamine penta (methylene phosphonic acid) (DETPMP); bis-hexamethylene triamine pentakis (methylene phosphonic acid); diglycol amine phosphonate (DGA phosphonate); 1-hydroxyethylidene 1,1-diphosphonate (HEDP phosphonate); bisaminoethylether phosphonate (BAEE phosphonate. amino tri(methylenephosphonic acid) (ATMP), 2-hydroxyethyliminobis (methylenephosphonic acid) (HEBMP), ethylene diamine tetra(methylene phosphonic acid); ethylene diamine tetra(methylene phosphonic acid) derivatives; as well as mixtures thereof.

In another embodiment, the organophosphorus surfactant may be a phosphino derivatized or partially neutralized carboxylate polymer salt of approximate number average molecular weight from about 500 to 20,000, typically from about 1,000 to 6,000.

Exemplary phosphino carboxylic salts include:
homopolymeric phosphinopoly(meth)acrylic acids of the formula:

(III)

wherein:
$R^1$ is a residue —OX wherein X is selected from a hydrogen atom, an alkali metal or alkaline earth metal cation, an ammonium ion or an amine residue;
$R^2$ is a polymeric residue comprising at least one unit of formula (IV):

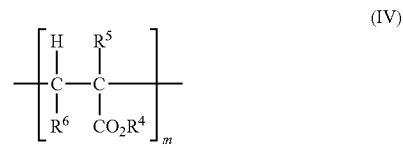

(IV)

and optionally at least one unit of formula (V):

(V)

$R^3$ is selected from a residue —OX wherein X is selected from a hydrogen atom, an alkali metal or alkaline earth metal cation, an ammonium ion or an amine residue;
a hydrogen atom; or a polymeric residue comprising at least one unit of formula (IV) and optionally at least one unit of formula (V);
$R^4$ is selected from a hydrogen atom; an alkali metal cation, an ammonium ion or an amine residue; an alkyl group having from 1 to 4 carbon atoms; or a phenyl group;
$R^5$ is selected from: a hydrogen atom; a methyl group or a group —CO$^2$R$^7$, $R^7$ is an alkyl group comprising from 1 to 4 carbon atoms;

$R^6$ is selected from a hydrogen atom; an alkyl group comprising 1 to 4 carbon atoms optionally substituted by a hydroxyl group; or a group —$CO_2R^8$ wherein $R^8$ is selected from a hydrogen atom or an alkyl group comprising from 1 to 4 carbon atoms;

$R^9$ is selected from a hydrogen atom; a methyl group; or a group —$CO_2R^{12}$ wherein $R^{12}$ is selected from a hydrogen atom or an alkyl group comprising from 1 to 8 carbon atoms;

$R^{10}$ is selected from a hydrogen atom; an alkyl group comprising from 1 to 4 carbon atoms; a hydroxymethyl group; or a group —$CO_2R^{13}$ wherein $R^{13}$ is selected from a hydrogen atom or an alkyl group comprising from 1 to 8 carbon atoms;

$R^{11}$ is selected from: a sulfonate containing group; a residue —$CO_2R^{14}$ wherein $R^{14}$ is selected from a hydrogen atom or an alkyl group comprising from 1 to 4 carbon atoms; a straight or branched alkyl residue having 1 to 8 carbon atoms optionally substituted by one to three carboxylic acid groups; a phenyl residue; an acetoxy residue; hydroxymethyl; an acetoxymethyl residue; —$SO_3M$, —$CH_2SO_3M$, —$PO_3M_2$ or $PO_3M'_2$ in which M is selected from hydrogen, an alkali metal or an alkaline earth metal and each M' is M or $C_1$-$C_4$ alkyl; a residue —$CONR^{15}R^{16}$ wherein $R^{15}$ and $R^{16}$ are the same or different and each is selected from hydrogen, a straight or branched chain alkyl residue having 1 to 8 carbon atoms, hydroxymethyl or a residue —CH(OH)—$CO_2M$, —$C(CH_3)_2CH_2SO_3M$ or —$C(CH_3)_2CH_2PO_3M_2$ in which M is selected from hydrogen, an alkali metal or alkaline earth metal; or —$N(R^{17})COCH_3$ in which $R^{17}$ is selected from hydrogen or $C_1$-$C_4$ straight or branched chain alkyl;

m is from 1 to 300, preferably 1 to 200, more preferably 5 to 100;

n is from 1 to 300, preferably 1 to 200, more preferably 5 to 100;

n+m is from 3 to 300, preferably 3 to 200, more preferably 5 to 100; and the ratio of n:m is from 99:1 to 1:99.

a homopolymeric phosphinopoly(meth) acrylic acid having the formula (VI):

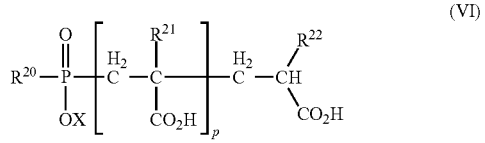

wherein:

X is selected from a hydrogen atom or an alkali metal cation;

$R^{21}$ is a hydrogen atom or a methyl group;

$R^{22}$ is selected from a hydrogen atom or a methyl group; and $R^{20}$ is selected from a hydrogen atom or a group of formula (VII):

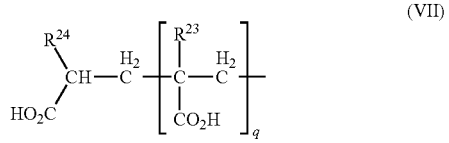

wherein $R^{23}$ is selected from a hydrogen atom or a methyl group, $R^{24}$ is selected from a hydrogen atom or a methyl group and p and q are integers; and a phosphino polymer of the formula (VIII):

wherein:

$R^{1a}$ is an —OX residue and X is selected from hydrogen or an alkali metal cation;

$R^{2a}$ is a copolymer of acrylic acid and 2-acrylamido-2-methylpropane sulfonic acid (AMPS) in a molar ratio of from 1:20 to 20:1; and $R^{3a}$ is a copolymer of acrylic acid and 2-acrylamido-2-methylpropane sulfonic acid (AMPS) or an —OX residue wherein X is selected from hydrogen or an alkali metal cation in a molar ratio of from 1:20 to 20:1.

a phosphino polymer having formula (IX):

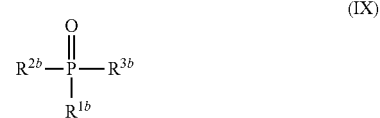

wherein:

$R^1$ is an —OX residue wherein X is selected from hydrogen or an alkali metal cation;

$R^2$ is a homopolymer of acrylic acid or methacrylic acid;

$R^3$ is a homopolymer of acrylic acid or methacrylic acid or is an —OX residue wherein X is selected from hydrogen or an alkali metal cation.

Typically, the amount of organophosphorus surfactant in the total treatment fluid volume ranges from 0 to 100 gallons per thousand gallons of total treatment fluid volume. In one embodiment, the amount of organophosphorus surfactant in the total fluid volume is about 10 gpt.

In addition to the organophosphorus surfactant, the aqueous delayed acid system may contain the acid retarder. In addition to disrupting hydrogen bonding of the water or brine of the treatment fluid, limiting diffusion of protons and the rate of disassociation of the acid, the acid retarder slows down the rate at which the acid solution reacts with carbonate-minerals. The capacity of the acid is not compromised by slowing the reactivity of the acid towards the carbonate-mineral surfaces. Slowing the rate of reaction further allows deeper penetration as well as convective transport of the acid into the formation compared to fluids containing (the same equivalent amount and molality) of acid only, thus increasing the formation permeability.

Exemplary bifunctional organic compounds are those containing both a quaternary phosphonium or ammonium group and a —OH group. In some instances, the bifunctional organic compound contains more than one quaternary phosphonium or ammonium group and/or more than one —Oh group.

Preferred bifunctional organic compounds are phosphonium hydroxyl $C_1$-$C_4$ alkyl salts such as phosphonium chloride and sulfate based compounds. Exemplary of such bifunctional organic compounds are the tetrakishydroxymethyl phosphonium salts, such as tetrakis(hydroxymethyl) phosphonium chloride of the structure (X):

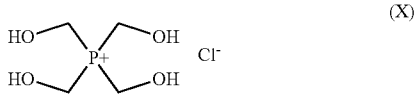

Exemplary bifunctional organic compounds are those containing at least one ammonium moiety and at least one —OH group. These include, for instance, choline chloride, as well as hydroxyethyl ammonium salts like trimethyl hydroxyethyl ammonium chloride as well as hydroxy ammonium salts greater than or equal to five to fifteen carbon atoms like bis(hydroxyethyl)dimethyl ammonium chloride and salts of the structure (XI):

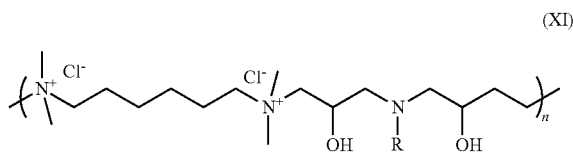

R = ethyl, butyl, hexyl, dodecyl, octadecyl

Other exemplary bifunctional organic compounds include salts of nitrogen containing heterocyclic rings, like salts of imidazolines, including alkyl substituted imidazolium salts. Exemplary imidazoline salts are 1-butyl-3-methylimidazolium chloride; 1-ethyl-3-methylimidazolium chloride; 1-ethyl-3-methylimidazolium acetate; N-methylpyrrolinium acetate; N-methylpyrrolinium chloride; 1-butyl-4-methylpyridinium chloride; 1,3-dimethylimidazolium dimethylphosphate; 1-ethyl-3-methylimidazolium ethyl sulfate; 1-ethyl-3-methylimidazolium methylsulfonate; 1-ethyl-3-methylimidazolium hydroxide; 1-butyl-3-methylimidazolium methanesulfonate; methyl-tri-n-butylammonium methyl sulfate; 1,2,4-trimethylpyrazolium methyl sulfate; 1-ethyl-2,3-dimethylimidazolium ethyl sulfate; 1,2,3-trimethylimidazolium methyl sulfate; methylimidazolium chloride; methylimidazolium hydrogen sulfate; 1-ethyl-3-methylimidazolium hydrogen sulfate; 1-butyl-3-methylimidazolium hydrogen sulfate; 1-butyl-3-methylimidazolium acetate; 1-butyl-3-methylimidazolium methyl sulfate; 1-ethyl-3-methylimidazolium thiocyanate; 1-butyl-3-methylimidazolium thiocyanate; choline acetate; choline salicylate; 1-ethyl-3-methylimidazolium nitrate, 1-ethyl-3-methylimidazolium tosylate, 1-ethyl-3-methylimidazolium bromide, 1-allyl-3-methylimidazolium chloride, 1-methyl-3-propylimidazolium iodide, 1-butyl-1-methylpyrrolidinium dicyanamide and tributylmethylphosphonium methyl sulfate.

The acid retarder is added to the aqueous delayed acid system in an amount up to its solubility limit in the aqueous delayed acid system. When present, the concentration of acid retarder may range from about 5 to 80 weight percent of the total weight of the water fraction of the total treatment fluid. In an embodiment, the amount of bifunctional organic compound may be from 15 to 30 weight percent and the amount of urea may be from 15 to 30 weight percent.

The aqueous delayed acid system may contain, in addition to the acid retarder, another retarding agent for reducing acid activity. Non-limiting examples of such retarding agents include salt compounds having a cation selected from one or more of lithium, sodium, potassium, rubidium, cesium, beryllium, magnesium, calcium, strontium, barium, scandium, yttrium, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, mercury, boron, aluminum, gallium, indium, thallium, tin and an anion selected from one or more of fluoride, chloride, bromide, iodide, sulfate, bisulfate, sulfite, and bisulfite nitrate.

Further, the aqueous composition may be combined with one or more other additives known to those of skill in the art, such as, but not limited to, corrosion inhibitors, scale inhibitors, demulsifiers, foaming agents, hydrogen sulfide scavengers, reducing agents and/or chelants, and the like. When present, such component(s) may be present in an amount of from about 0.2% to about 3% by total weight of the treatment fluid.

The aqueous composition may be prepared by mixing the acid with the organophosphorus surfactant (when present) and water and, when present, the acid retarder along with optional additives. The acidizing fluid may then be pumped into the formation at matrix rates. Downhole temperatures may range from 120° F. to as high as 250° F. and in some cases as high as 350° F. When pumping downhole, the acid of the aqueous delayed acid system does not typically react initially with the formation. The well may be shut-in for periods which may range from at least 30 minutes with shorter times at in-situ temperatures higher than 150° F. As such, the acid of the aqueous delayed acid system can penetrate deeper into the rock matrix. As such, the aqueous delayed acid system is ideally suited for deep matrix acidizing.

EXAMPLES

The following examples are illustrative of some of the embodiments referenced herein. Other embodiments within the scope of the claims will be apparent to one skilled in the art from consideration of the description provided. It is intended that the specification, together with the examples, be considered exemplary only, with the scope and spirit of the invention being indicated by the claims which follow.

All percentages set forth in the Examples are given in terms of weight units except as may otherwise be indicated Example 1. An acid mixture containing choline chloride, urea and a phosphobteaine surfactant was prepared. The acid mixture had a final acid concentration of 28 wt % HCl, 20 wt % choline chloride, 20 wt % urea, and 10 gpt surfactant. A phosphobetaine surfactant prepared by the reaction of phosphated mono-chloro glycerine (chloro-glyceryl phosphate) reacted with tertiary amine (cocamidopropyl dimethylamine).

A static carbonate dissolution test was then conducted to measure the calcium carbonate dissolution in the acid solution. Indiana limestone disks of 1.5 in. in diameter and 0.75 in. in length were immersed in 100 ml of the acid solution for 10 minutes. The disk weights were measured before and after the test to measure the amount of the calcium carbonate dissolved using the acid solution. A decrease in the amount of the calcium carbonate dissolved was indicative of lower acid reactivity. The tests were conducted at 175° F. The retarded characteristics of the 28 wt % acid solution containing the bifunctional organic compound (choline chloride), urea, and surfactant compared to the regular 28 wt % HCl are illustrated in FIG. 1 where 82% of the calcium carbonate is shown to have been dissolved using regular 28 wt % HCl compared to 7.75% of calcium carbonate dissolved using the 28 wt % acid solution containing the bifunctional organic compound (choline chloride), urea, and surfactant.

Figure 2:
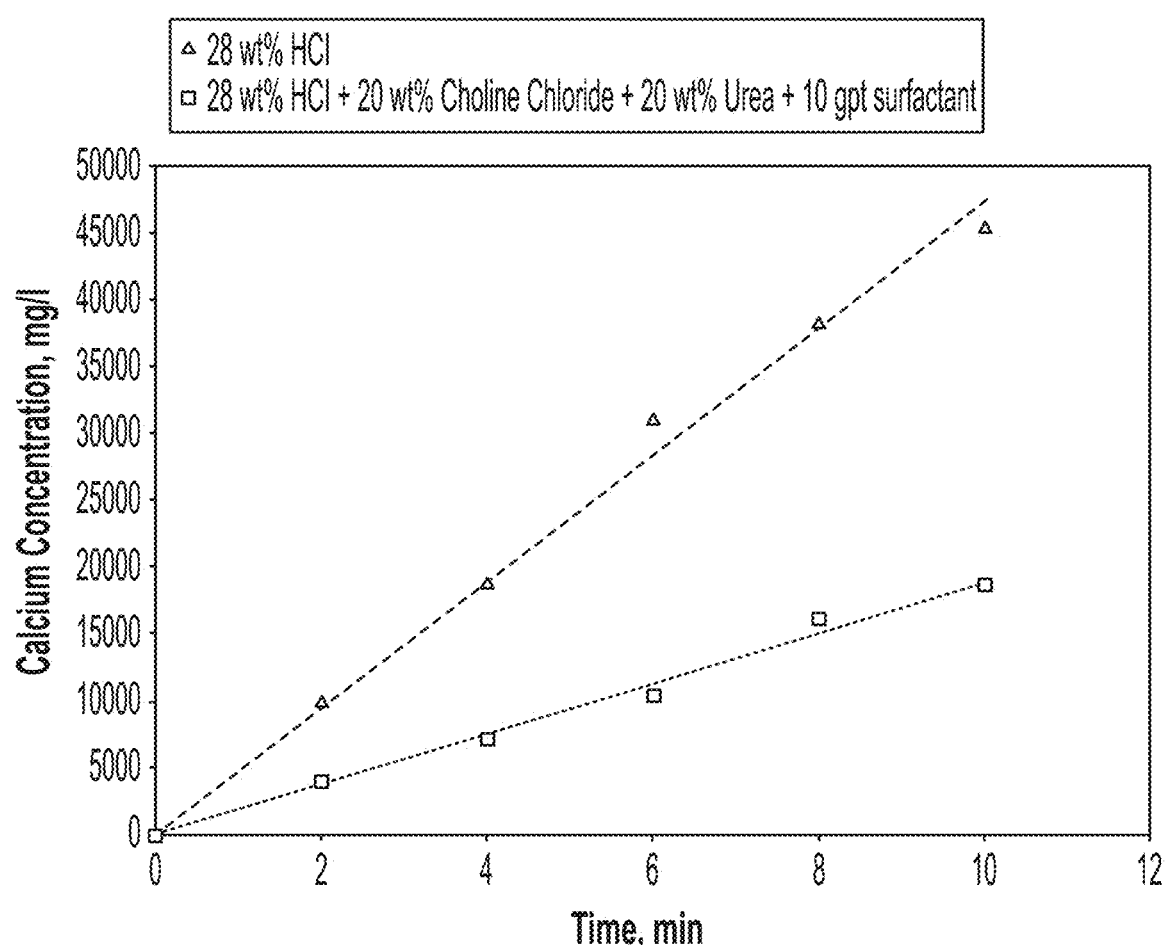
FIG. 2 contrasts dissolved calcium concentration vs. time for the reaction between an aqueous acidizing solution containing only 28 weight percent HCl and Indiana limestone with an aqueous acidizing solution containing 28 weight percent % HCl, choline chloride, urea, and an amino organophosphorus surfactant and Indiana limestone at 1000 rpm and 225° F.
Figure 3:
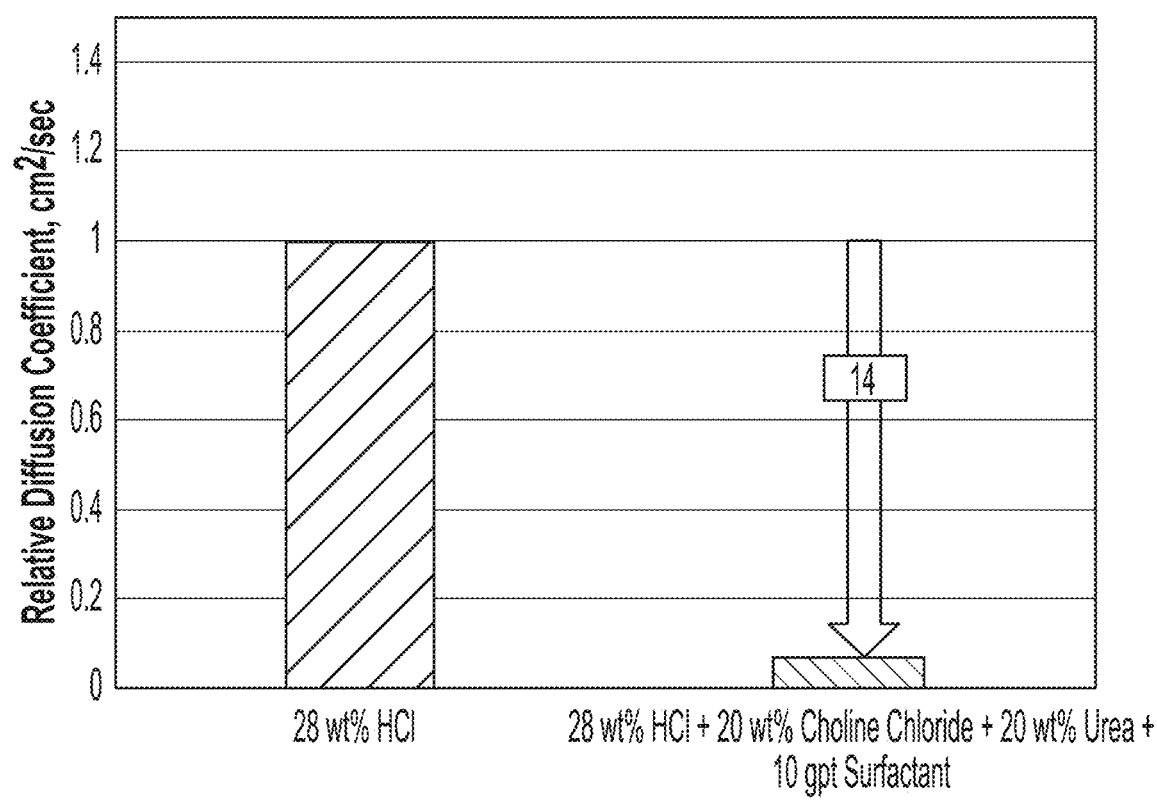
FIG. 3 illustrates relative diffusion coefficient of an aqueous acidizing solution containing 28 weight percent HCl, choline chloride, urea, and an amino organophosphorus surfactant.

Example 2. Rotating disk experiments were conducted to measure the rate of reaction of the acid solution of Example 1 with carbonates. Indiana limestone disks of 1.5 in. in diameter and 0.75 in. in length were used in the rotating disk experiments. The experiments were conducted by rotating the disk in the acid solution at temperature of 225° F. and at a disk rotational speed of 1000 rpm. Compressed nitrogen was used to pressurize the reactor vessel of the rotating disk apparatus to 1,200 psi to keep the evolved $CO_2$ from the acid-rock reaction in solution. Samples of 5 $cm^3$ each were collected at equal time intervals of 2 min for 10 min. Calcium concentration in the collected samples was measured using inductively coupled plasma mass spectrometer. The rate of the acid solution reaction with calcium carbonate was then determined from the rate of the change of the calcium concentration with time. FIG. 2 illustrates rate of change of the calcium concentration with time for the 28 wt % HCl acid solution containing the bifunctional organic compound (choline chloride), urea, and surfactant compared to the regular 28 wt % HCl for 10 minutes. As illustrated, the 28 wt % HCl acid solution containing the bifunctional organic compound (choline chloride), urea, and surfactant had a slower reaction rate compared to the regular 28 wt % HCl. Diffusion coefficient measured the diffusion of the $H^+$ protons to the surface of the rock. Acids with lower diffusion coefficient are more retarded than acids with higher diffusion coefficient. The diffusion coefficient was calculated from the rotating disk experiments results. FIG. 3 shows the relative diffusion coefficient of the 28 wt % HCl acid solution containing organic compound, urea and surfactant.

Figure 4:
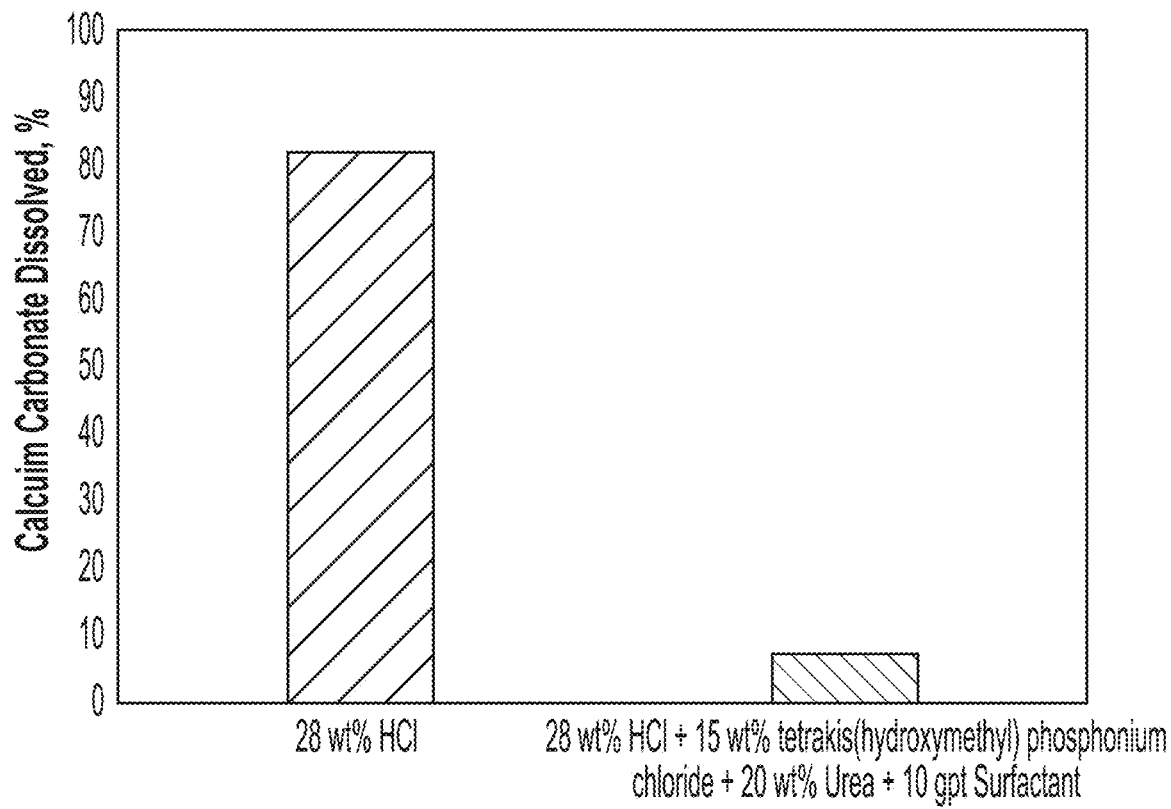
FIG. 4 contrasts calcium carbonate dissolved using an aqueous acidizing solution containing only 28 weight percent HCl with an aqueous acidizing solution containing 28 weight percent HCl, tetrakis(hydroxymethyl) phosphonium chloride, urea, and an amino organophosphorus surfactant.

Example 3. Example 1 was repeated except choline chloride was replaced with tetrakis(hydroxymethyl) phosphonium chloride of structure (X). The static carbonate dissolution test was then conducted under the same test conditions to measure the calcium carbonate dissolution in the acid solution. The retarded characteristics of the 28 wt % acid solution containing organic salt (phosphonium chloride), urea, and surfactant compared to 28 wt % HCl are illustrated in FIG. 4 where 82% of the calcium carbonate is shows to have been dissolved using regular 28 wt % HCl compared to 8.2% of calcium carbonate dissolved using the 28 wt % acid solution containing organic salt (phosphonium chloride), urea, and surfactant.

Figure 5:
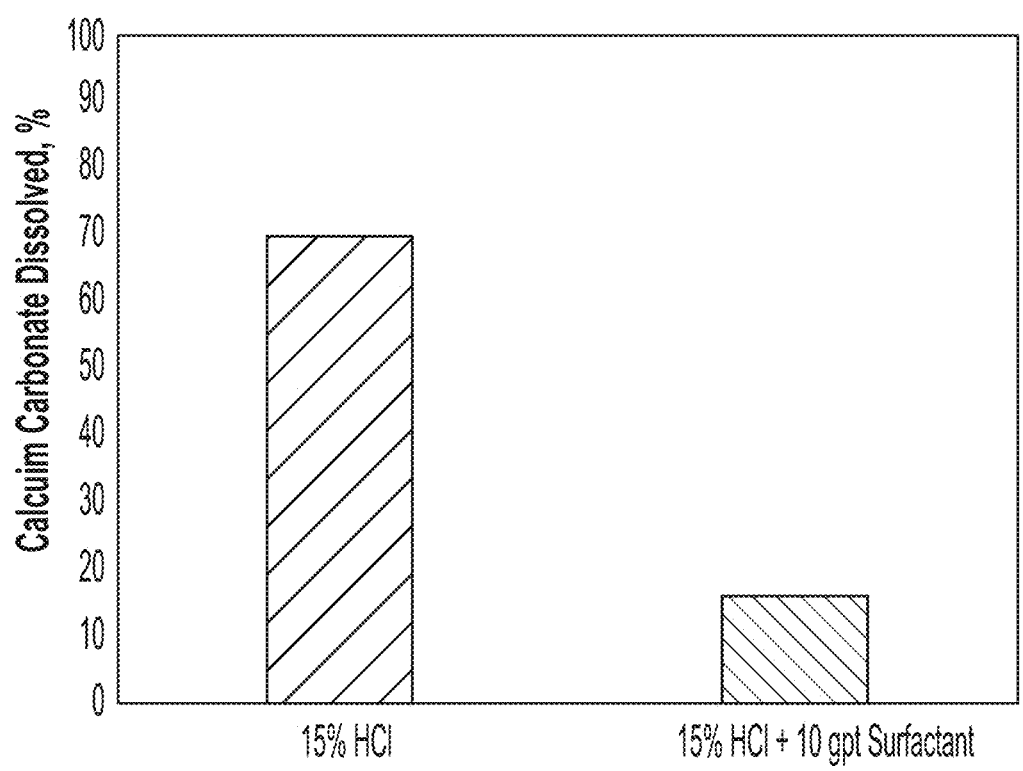
FIG. 5 contrasts calcium carbonate dissolved using an aqueous acidizing solution containing 15 weight percent HCl with an aqueous acidizing solution containing 28 weight percent HCl and an amino organophosphorus surfactant FIG. 6 contrasts the difference in pore volume to breakthrough of an acidizing solution containing 28 weight percent HCl, an organophosphorus surfactant, choline chloride, and urea with an acidizing solution containing only 28 weight percent HCl.

Example 4. A phosphobetaine surfactant was add concentrated hydrochloric acid (28 weight percent) at 10 gpt (gallon per thousand gallon) concentration. A static carbonate dissolution test was then conducted to measure the calcium carbonate dissolution in the acid solution. Indiana limestone disks of 1.5 in. in diameter and 0.75 in. in length were immersed in 100 ml of the acid solution for 10 minutes. The disk weights were measured before and after the test to measure the amount of the calcium carbonate dissolved using the acid solution. A decrease in the amount of the calcium carbonate dissolved was indicative of lower acid reactivity. The test was conducted at 175° F. The retarded characteristics of the 28 wt % acid solution and surfactant compared to the regular 28 wt % HCl are illustrated in FIG. 5 where 82% of the calcium carbonate is shown to have been dissolved using regular 28 wt % HCl compared to 16% of calcium carbonate dissolved using the 28 wt % acid solution containing the amino organophosphorus surfactant.

Figure 6:
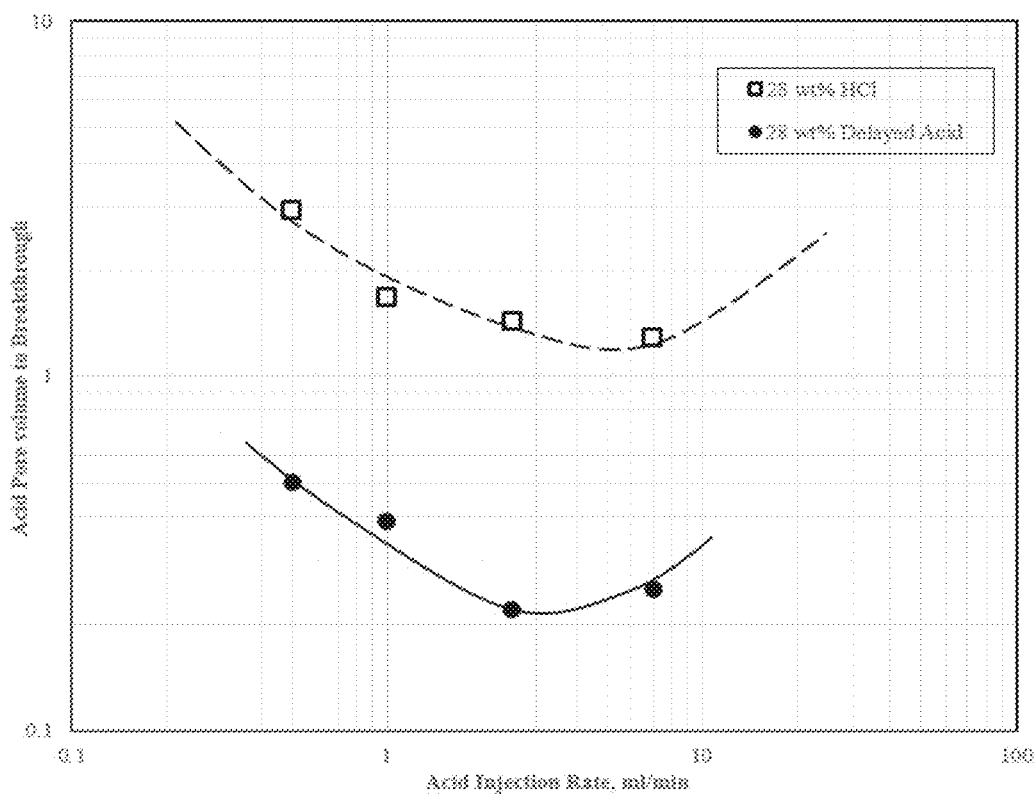
Figure 7:
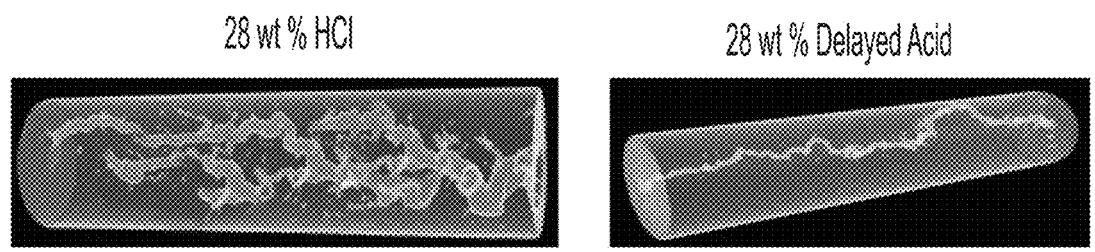
FIG. 7 contrasts wormhole creation from an acidizing solution containing 28 weight percent HCl, an organophosphorus surfactant, choline chloride and urea with an acidizing solution containing only 28 weight percent HCl.

Example 5. To evaluate the acid performance, Acid-$PV_{bt}$ (pore volume to breakthrough) experiments were conducted. In these experiments, Indiana limestone core samples of 1.5" in diameter and 6" in length were loaded in a core holder and heated to 225° F. A back pressure of 1100 psi was applied to keep most of the carbon dioxide generated during the test in solution. An overburden pressure of 2000 psi was applied to prevent the injected fluid from bypassing the core. The acid was then injected through the core until acid breakthrough. The pressure drop was monitored across the core and acid breakthrough was determined by a sudden decrease in the pressure drop to almost zero. Four experiments were conducted where the acid was injected at constant rates of 0.5, 1, 2.5, and 7 $cm^3$/min. The acid pore volume to breakthrough at different injection rates is illustrated in FIG. 6 for an acidizing solution containing 28 wt % HCl acid and an acidizing solution prepared by the procedure set forth in Example 1 and containing 28 wt % HCl acid, choline chloride, urea, and phosphobetaine surfactant. The acidizing solution containing 28 wt % HCl, choline chloride, urea, and organophosphorus surfactant needed significantly less acid pore volumes to breakthrough compared to the acidizing solution containing only 28 wt % HCl acid. At the optimum injection rate, where the acid needs the minimum pore volumes to breakthrough and creates dominant wormhole through the entire length of the core, the 28 wt % HCl acidizing solution needed 1.2 acid $PV_{bt}$ compared to only 0.2 acid $PV_{bt}$ for the acidizing solution containing 28 wt % HCl, choline chloride, urea, and organophosphorus surfactant. Moreover, at the optimum injection rate, the acidizing solution containing 28 wt % HCl acid, choline chloride, urea, and surfactant created narrow and dominant wormhole through the entire core length while the acidizing solution containing only 28 wt. % HCl acid created highly branched wormhole structure (FIG. 7).

Figure 8:
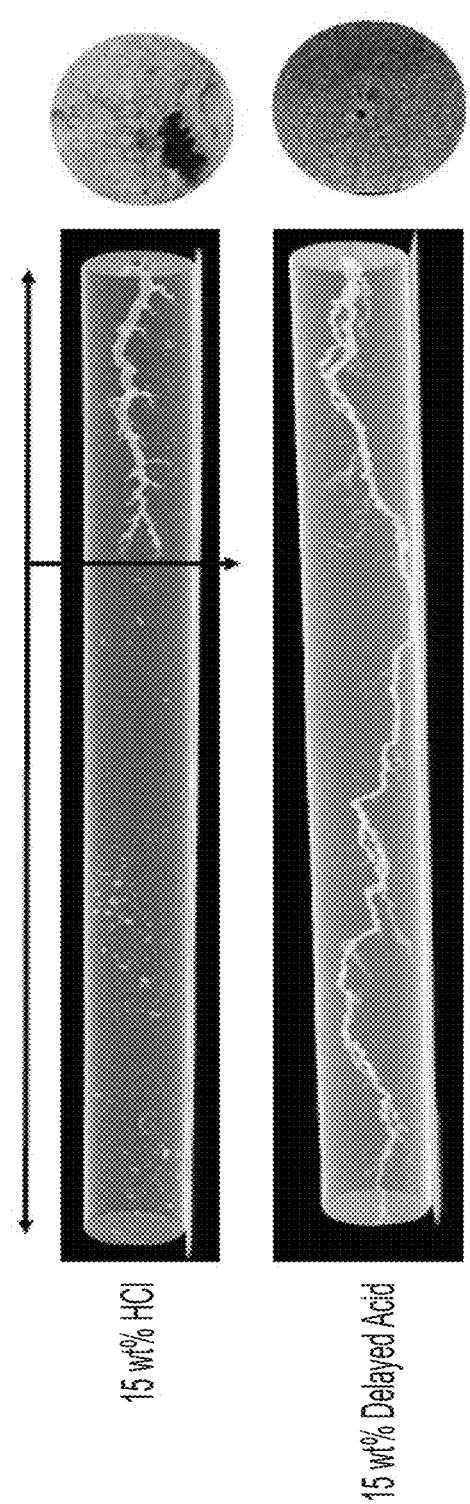
FIG. 8 demonstrates efficiency in stimulation with an acidizing solution containing 15 weight percent HCl, choline chloride, urea and an organophosphorus surfactant versus an acidizing solution containing only 15 weight percent HCl.

Example 6. The retardation performance of two acidizing solutions were evaluated wherein equal volumes (0.275 pore volumes) of an acidizing solution containing only 15 wt % HCl acid and an acidizing solution containing 15 wt % HCl acid, choline chloride, urea, and organophosphorus surfactant (prepared by the procedure set forth in Example 1) were injected into 20" in length and 1.5" in diameter Indiana Limestone core sample at 275° F. The acidizing solution containing only 15 wt % HCl acid created a wormhole to 25% of the entire core length before completely spending while the acidizing solution containing 15 wt % HCl acid, choline chloride, urea, and organophosphorus surfactant created wormhole through the entire length of the core sample (illustrated in FIG. 8). The delayed or retarded acidizing solution containing HCl acid, choline chloride, urea and organophosphorus surfactant penetrated deeper into the formation compared to the acidizing solution containing only HCl acid, before completing spending. In particular, the core face for the core sample treated with the acidizing solution containing only 15 wt % HCl acid showed face dissolution while the core face for the core sample treated with the acidizing solution containing 15 wt % HCl acid, choline chloride, urea, and organophosphorus surfactant showed a dominant wormhole entry. The increase in efficiency from results above then determines that more deeper and efficient stimulation per gallon of acid used is obtained with the acidizing solution containing 15 wt % HCl acid, choline chloride, urea, and surfactant than the acidizing solution containing only 15 wt % HCl acid.

Embodiment 1. An acidizing composition for use in acidizing a subterranean formation comprising, as a first member, an inorganic or organic acid and, as a second member (1) an organophosphorus surfactant selected from the group consisting of amino phosphonates and phosphino carboxylates; and/or (2) an acid retarder of (a) urea or a urea derivative and (b) a bifunctional organic compound comprising (i) at least one quaternary phosphonium or ammonium moiety and at least one —OH group; or (ii) a salt of a nitrogen containing heterocyclic ring.

Embodiment 2. The acidizing composition of Embodiment 1, wherein the second member contains the organophosphorus surfactant but not the acid retarder.

Embodiment 3. The acidizing composition of Embodiment 1, wherein the second member contains both the organophosphorus surfactant and the acid retarder.

Embodiment 4. The acidizing composition of Embodiment 1, wherein the second member contains the acid retarder but not the organophosphorus surfactant.

Embodiment 5. A method of acidizing a subterranean formation comprising (a) contacting said formation with the acidizing composition of Embodiment 2 or 3; and (b) retarding the spending of the acid in the acidizing composition in the well by adsorbing onto the surface of the formation the organophosphorus surfactant.

Embodiment 6. A method of acidizing a subterranean carbonate formation comprising (a) introducing into a well penetrating the subterranean formation a fluid comprising the acidizing composition of any of Embodiments 1 to 4; and (b) enhancing the creation and penetration of wormholes by retarding or slowing down the spending of the acid.

Embodiment 7. A method of acidizing a subterranean formation comprising (a) pumping into the well penetrating the formation the acidizing composition of Embodiment 2 or 3; (b) adsorbing onto the surface of the formation the organophosphorus surfactant and limiting bonding sites for the acid; and (c) delaying spending of the acid in the acidizing fluid by the presence of the adsorbed organophosphorus surfactant on the formation surface.

Embodiment 8. A method of acidizing a subterranean formation penetrated by a well with the acidizing composition of any of Embodiments 2 to 4 comprising (a) combining water, the first member and the second member to form the aqueous acidizing fluid; (b) pumping the aqueous acidizing fluid into the well; and (c) delaying spending of the acid with the second member.

Embodiment 9. A method of reducing the reaction time for dissolution of a carbonate matrix during acidizing of the formation comprising (a) pumping into the well penetrating the formation the acidizing fluid of either Embodiment 3 or 4; and (b) decreasing transfer of the acid proton onto the surface of the formation.

Embodiment 10. The method of any of Embodiments 5 to 9, wherein the acidizing fluid is not an emulsion and is void of emulsifying agents.

Embodiment 11. The method of any of Embodiments 5 to 10, wherein the carbonate formation is limestone, chalk or dolomite.

Embodiment 12. The method of any of Embodiments 5 to 11, wherein the acid is an inorganic acid selected from the group consisting of hydrochloric acid, nitric acid, phosphoric acid, sulfuric acid, hydrofluoric acid, hydrobromic acid, perchloric acid and hydrogen iodide and mixtures thereof.

Embodiment 13. The method of Embodiment 12, wherein the inorganic acid is hydrochloric acid.

Embodiment 14. The method of any of claims 5 to 11, wherein the acid is an organic acid.

Embodiment 15. The method of Embodiment 14, wherein the acid is selected from the group consisting of alkanesulfonic acids, arylsulfonic acids, acetic acid, formic acid, alkyl carboxylic acids, acrylic acid, lactic acid, glycolic acid, malonic acid, fumaric acid, glutamic acid, citric acid, tartaric acid, glutamic acid-N,N-diacetic acid (GLDA), hydroxyl ethylene diameinetriacetic acid (HDEDTA), N-hydroxyethyl-N, N', N'-ethylenediaminetriacetic acid (HEDTA), hydroxyethyliminodiacetic acid (HEIDA), diethylenetriaminepentaacetic acid (DTPA) and cyclohexylenediaminetetraacetic acid (CDTA) and mixtures thereof.

Embodiment 16. The method of any of Embodiments 5 to 15, wherein the organophosphorus surfactant is an amino phosphonate.

Embodiment 17. The method of any of Embodiments 5 to 15, wherein the organophosphorus surfactant has at least one —OH group, at least one alkyl group, a phosphonium group and at least one ammonium group.

Embodiment 18. The method of Embodiment 16, wherein the organophosphorus surfactant is an amino phospholipid.

Embodiment 19. The method of Embodiment 18, wherein the phospholipid is of the structure (I):

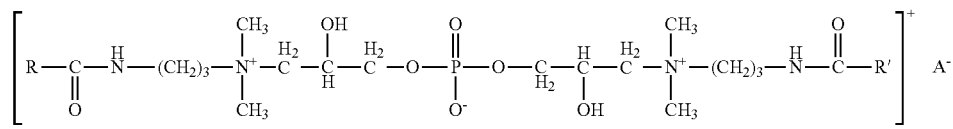

wherein R and R' are $C_6$ to $C_{25}$ hydrocarbon groups and A is selected from the group consisting of halide, nitrate, sulfate, phosphate, anions of $C_1$ to $C_{10}$ organic acids and mixtures thereof.

Embodiment 20. The method of Embodiment 18, wherein the phospholipid comprises at least one fatty acid amidopropyl propylene glycol dimonium phosphate salt wherein the fatty acid is a $C_{10}$ $C_{25}$ fatty acid.

Embodiment 21. The method of Embodiment 18, wherein the phospholipid is a cocadmidopropyl PG-dimonium chloride phosphate salt or a ricinoleamidopropyl PG-dimonium chloride phosphate.

Embodiment 22. The method of Embodiment 18, wherein the phospholipid is a dilinoleamidopropyl PG-dimonium chloride phosphate.

Embodiment 23. The method of Embodiment 18, wherein the phospholipid is selected from the group consisting of sodium cocamidopropyl PG-dimonium chloride phosphate and sodium dilinoleamidopropyl PG-dimonium chloride phosphate or a mixture thereof.

Embodiment 24. The method of Embodiment 18, wherein the phospholipid is dimer dilinoleamido-propyl PG-dimonium chloride phosphate; linoleamidopropyl PG-dimonium chloride phosphate dilinoleamidopropyl PG-dimonium chloride phosphate as well as mixtures thereof.

Embodiment 25. The method of Embodiment 18, wherein the phospholipid is a 1-propanaminium, 3,3',3"-[phosphinylidynetris(oxy)]tris[N-(3-aminopropyl)-2-hydroxy-N,N-dimethyl-, N,N',N"-tri-$C_{6-18}$ acyl derivatives trichlorides.

Embodiment 26. The method of any of Embodiments 5 to 15, wherein the organophosphorus surfactant is an ester based phosphobetaine having a quaternized nitrogen.

Embodiment 27. The method of Embodiment 16, wherein the organophosphorus surfactant is an amino phosphonate of the formula (II):

$$R^1-C(O)O-(CH_2CH_2O)_a-(CH_2CH(CH_3)O)_b-(CH_2CH_2O)_c- \\ \quad\quad -P(O)-OCH_2-CH(OH)CH_2-\underset{\underset{CH_3}{|}}{\overset{\overset{CH_3}{|}}{N^+}}-R^2 \\ \quad\quad\; |\\ \quad\quad O^- $$ (II)

wherein:
- $R^1$ is alkyl or alkylene having between 7 and 21 carbon atoms;
- a, b and c are each independently integers ranging from 0 to 20, with the proviso that a+b+c be equal to or greater than 1;
- $R^2$ is selected from the group consisting of alkyl having 7 to 21 carbon atoms and $R^3$—C(O)—N(H)—(CH$_2$)$_2$— where $R^3$ is alkyl having 7 to 21 carbon atoms.

Embodiment 28. The method of any of Embodiments 5 to 15, wherein the organophosphorus surfactant is an oil soluble blend of a tertiary alkyl amine and an amino phosphonic acid.

Embodiment 29. The method of any of Embodiments 5 to 15, wherein the organophosphorus surfactant is an amino phosphonic acid selected from the group consisting of hexamethylene diamine tetrakis (methylene phosphonic acid); diethylene triamine tetra (methylene phosphonic acid); diethylene triamine penta (methylene phosphonic acid) (DETPMP); bis-hexamethylene triamine pentakis (methylene phosphonic acid); diglycol amine phosphonate (DGA phosphonate); 1-hydroxyethylidene 1,1-diphosphonate (HEDP phosphonate); bisaminoethylether phosphonate (BAEE phosphonate. amino tri(methylenephosphonic acid) (ATMP), 2-hydroxyethyliminobis (methylenephosphonic acid) (HEBMP), ethylene diamine tetra(methylene phosphonic acid); ethylene diamine tetra(methylene phosphonic acid) derivatives and mixtures thereof.

Embodiment 30. The method of any of Embodiments 5 to 15, wherein the organophosphorus surfactant is a phosphino derivatized or partially neutralized phosphinocarboxylate polymer of approximate number average molecular weight from about 500 to 20,000.

Embodiment 31. The method of Embodiment 30, wherein the organophosphorus surfactant is a phosphino carboxylate selected from the group consisting of:

(a) homopolymeric phosphinopoly(meth)acrylic acids of the formula:

$$R^2-\underset{\underset{R^1}{|}}{\overset{\overset{O}{\|}}{P}}-R^3$$ (III)

wherein:
- $R^1$ is a residue —OX wherein X is selected from a hydrogen atom, an alkali metal or alkaline earth metal cation, an ammonium ion or an amine residue;
- $R^2$ is a polymeric residue comprising at least one unit of formula (IV):

$$\left[\begin{array}{cc} H & R^5 \\ | & | \\ -C-C- \\ | & | \\ R^6 & CO_2R^4 \end{array}\right]_n$$ (IV)

and optionally at least one unit of formula (V):

$$\left[\begin{array}{cc} H & R^{10} \\ | & | \\ -C-C- \\ | & | \\ R^9 & R^{11} \end{array}\right]_n$$ (V)

- $R^3$ is selected from a residue —OX wherein X is selected from a hydrogen atom, an alkali metal or alkaline earth metal cation, an ammonium ion or an amine residue; a hydrogen atom; or a polymeric residue comprising at least one unit of formula (IV) and optionally at least one unit of formula (V);
- $R^4$ is selected from a hydrogen atom; an alkali metal cation, an ammonium ion or an amine residue; an alkyl group having from 1 to 4 carbon atoms; or a phenyl group;
- $R^5$ is selected from: a hydrogen atom; a methyl group or a group —CO$^2$R$^7$, $R^7$ is an alkyl group comprising from 1 to 4 carbon atoms;
- $R^9$ is selected from a hydrogen atom; a methyl group; or a group —CO$_2$R$^{12}$ wherein $R^{12}$ is selected from a hydrogen atom or an alkyl group comprising from 1 to 8 carbon atoms;
- $R^{10}$ is selected from a hydrogen atom; an alkyl group comprising from 1 to 4 carbon atoms; a hydroxymethyl group; or a group —CO$_2$R$^{13}$ wherein $R^{13}$ is selected from a hydrogen atom or an alkyl group comprising from 1 to 8 carbon atoms;
- $R^{11}$ is selected from: a sulfonate containing group; a residue —CO$_2$R$^{14}$ wherein $R^{14}$ is selected from a hydrogen atom or an alkyl group comprising from 1 to 4 carbon atoms; a straight or branched alkyl residue having 1 to 8 carbon atoms optionally substituted by one to three carboxylic acid groups; a phenyl residue; an acetoxy residue; hydroxymethyl; an acetoxymethyl residue; —SO$_3$M, —CH$_2$SO$_3$M, —PO$_3$M$_2$ or PO$_3$M'$_2$ in which M is selected from hydrogen, an alkali metal or an alkaline earth metal and each M' is M or C$_1$-C$_4$ alkyl; a residue —CONR$^{15}$R$^{16}$ wherein $R^{15}$ and $R^{16}$ are the same or different and each is selected from hydrogen, a straight or branched chain alkyl residue having 1 to 8 carbon atoms, hydroxymethyl or a residue —CH(OH)—CO$_2$M, —C(CH$_3$)$_2$CH$_2$SO$_3$M or —C(CH$_3$)$_2$CH$_2$PO$_3$M$_2$ in which M is selected from hydrogen, an alkali metal or alkaline earth metal; or —N(R$^{17}$)COCH$_3$ in which $R^{17}$ is selected from hydrogen or C$_1$-C$_4$ straight or branched chain alkyl;
- m is from 1 to 300;
- n is from 1 to 300;
- n+m is from 3 to 300; and
- the ratio of n:m is from 99:1 to 1:99;

(b) homopolymeric phosphinopoly(meth) acrylic acids of the formula (VI):

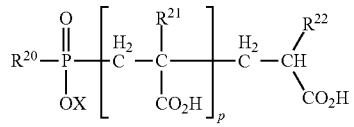

wherein:
X is selected from a hydrogen atom or an alkali metal cation;
$R^{21}$ is a hydrogen atom or a methyl group;
$R^{22}$ is selected from a hydrogen atom or a methyl group; and
$R^{20}$ is selected from a hydrogen atom or a group of formula (VII):

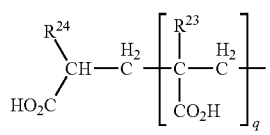

wherein $R^{23}$ is selected from a hydrogen atom or a methyl group, $R^{24}$ is selected from a hydrogen atom or a methyl group; and
p and q are integers; and
(a) phosphino polymers of the formula (VIII):

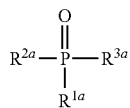

wherein:
$R^{1a}$ is an —OX residue and X is selected from hydrogen or an alkali metal cation;
$R^{2a}$ is a copolymer of acrylic acid and 2-acrylamido-2-methylpropane sulfonic acid (AMPS) in a molar ratio of from 1:20 to 20:1; and
$R^{3a}$ is a copolymer of acrylic acid and 2-acrylamido-2-methylpropane sulfonic acid (AMPS) or an —OX residue wherein X is selected from hydrogen or an alkali metal cation in a molar ratio of from 1:20 to 20:1.

Embodiment 32. The method of any of Embodiments 5 to 31, wherein, the bifunctional organic compound is a phosphonium hydroxyl $C_1$-$C_4$ alkyl salt.

Embodiment 33. The method of Embodiment 32, wherein the bifunctional organic compound is a phosphonium chloride or a sulfate based compound.

Embodiment 34. The method of Embodiment 32, wherein the bifunctional organic compound is a tetrakishydroxymethyl phosphonium salt.

Embodiment 35. The method of any of Embodiment 5 to 31, wherein the bifunctional organic compound contains both quaternary ammonium or phosphonium and an alcohol.

Embodiment 36. The method of Embodiment 35, wherein the bifunctional organic compound is choline chloride.

Embodiment 37. The method of any of Embodiments 5 to 31, wherein the bifunctional organic compound is a hydroxyethyl ammonium salt.

Embodiment 38. The method of Embodiment 37, wherein the bifunctional organic compound is trimethyl hydroxyethyl ammonium chloride.

Embodiment 39. The method of any of Embodiments 5 to 31, wherein the bifunctional organic compounds is a salt of a nitrogen containing heterocyclic ring.

Embodiment 40. The method of Embodiment 39, wherein the bifunctional organic compound is a salt of an imidazoline.

Embodiment 41. The method of Embodiment 40, wherein the bifunctional organic compound is selected from the group consisting of 1-butyl-3-methylimidazolium chloride; 1-ethyl-3-methylimidazolium chloride; 1-ethyl-3-methylimidazolium acetate; N-methylpyrrolinium acetate; N-methylpyrrolinium chloride; 1-butyl-4-methylpyridinium chloride; 1,3-dimethylimidazolium dimethylphosphate; 1-ethyl-3-methylimidazolium ethyl sulfate; 1-ethyl-3-methylimidazolium methylsulfonate; 1-ethyl-3-methylimidazolium hydroxide; 1-butyl-3-methylimidazolium methanesulfonate; methyl-tri-n-butylammonium methyl sulfate; 1,2,4-trimethylpyrazolium methyl sulfate; 1-ethyl-2,3-dimethylimidazolium ethyl sulfate; 1,2,3-trimethylimidazolium methyl sulfate; methylimidazolium chloride; methylimidazolium hydrogen sulfate; 1-ethyl-3-methylimidazolium hydrogen sulfate; 1-butyl-3-methylimidazolium hydrogen sulfate; 1-butyl-3-methylimidazolium acetate; 1-butyl-3-methylimidazolium methyl sulfate; 1-ethyl-3-methylimidazolium thiocyanate; 1-butyl-3-methylimidazolium thiocyanate; choline acetate; choline salicylate; 1-ethyl-3-methylimidazolium nitrate, 1-ethyl-3-methylimidazolium tosylate, 1-ethyl-3-methylimidazolium bromide, 1-allyl-3-methylimidazolium chloride, 1-methyl-3-propylimidazolium iodide, 1-butyl-1-methylpyrrolidinium dicyanamide and tributylmethylphosphonium methyl sulfate.

Embodiment 42. The method of any of Embodiments 5 to 41, wherein the viscosity of the aqueous delayed acid system is from about 0.5 cP to about 10 cP, measured on a Model 35 Fann viscometer having a R1B1 rotor and bob assembly rotating at 300 rpm at 225° F.

What is claimed is:
1. An acidizing composition for use in acidizing a subterranean formation comprising, as a first member, an inorganic or organic acid and, as a second member:
    A. an organophosphorus surfactant selected from the group consisting of amino phosphonates and phosphino carboxylates; and
    B. an acid retarder of (a) urea or a urea derivative and (b) a bifunctional organic compound comprising (i) at least one quaternary ammonium moiety and at least one —OH group;
wherein the organophosphorus surfactant, in the presence of the acid retarder, is capable of being adsorbed onto a surface of the subterranean formation.

2. A method of treating a subterranean formation penetrated by a well comprising:
    (a) stimulating the formation with an acidizing composition comprising:
        (i) an organophosphorus surfactant selected from the group consisting of amino phosphonates and phosphino carboxylates; and
        (ii) an acid retarder of (a) urea or a urea derivative and (b) a bifunctional organic compound comprising (i) at least one quaternary ammonium moiety and at least one —OH group; and
    (b) enhancing permeability of the formation with the acidizing composition.

3. The method of claim 2, wherein the acidizing composition contains both the organophosphorus surfactant and the acid retarder.

4. The method of claim 2, comprising pumping the acidizing composition into the well at a pressure sufficient to create or enhance a fracture and reacting the acid with the formation to create conductive channels.

5. The method of claim 2, comprising pumping the acidizing composition into the well at a pressure lower than that which induces creation of a fracture and creating conductive branched flow channels within the formation.

6. The method of claim 2, wherein the organophosphorus surfactant has at least one —OH group, at least one alkyl group, a phosphonium group and at least one ammonium group.

7. The method of claim 2, wherein the organophosphorus surfactant is an ester based phosphobetaine having a quaternized nitrogen.

8. The method of claim 2, wherein the organophosphorus surfactant is an amino phosphonic acid, a phosphino carboxylate or a phosphino derivatized or partially neutralized phosphinocarboxylate polymer of approximate number average molecular weight from about 500 to 20,000 or an oil soluble blend of a tertiary alkyl amine and an amino phosphonic acid.

9. The method of claim 2, wherein the bifunctional organic compound contains both quaternary ammonium and an alcohol.

10. The method of claim 9, wherein the bifunctional organic compound is choline chloride.

11. The method of claim 2, wherein the bifunctional organic compound is a hydroxyethyl ammonium salt.

12. The method of claim 11, wherein the bifunctional organic compound is trimethyl hydroxyethyl ammonium chloride.

13. The method of claim 2, wherein the acidizing composition is an aqueous system comprising from 15 to 30 weight percent urea.

14. The method of claim 2, wherein the organophosphorus surfactant is an amino phosphonate.

15. The method of claim 14, wherein the organophosphorus surfactant is an amino phosphonate of the formula (II):

(II)

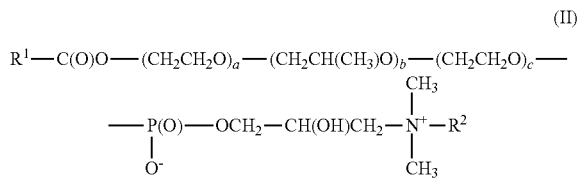

wherein:
R$^1$ is alkyl or alkylene having between 7 and 21 carbon atoms;

a, b and c are each independently integers ranging from 0 to 20, with the proviso that a+b+c be equal to or greater than 1;

R$^2$ is selected from the group consisting of alkyl having 7 to 21 carbon atoms and R$^3$—C(O)—N(H)—(CH$_2$)$_2$— where R$^3$ is alkyl having 7 to 21 carbon atoms.

16. The method of claim 14, wherein the organophosphorus surfactant is an amino phospholipid.

17. The method of claim 16, wherein the phospholipid is of the structure:

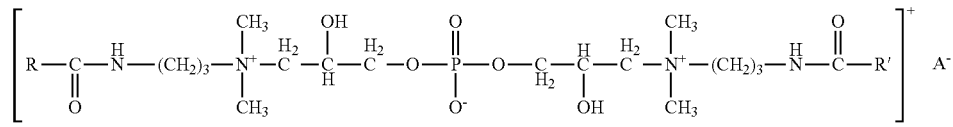

wherein R and R' are C$_6$ to C$_{25}$ hydrocarbon groups and A is selected from the group consisting of halide, nitrate, sulfate, phosphate, anions of C$_1$ to C$_{10}$ organic acids and mixtures thereof.

18. The method of claim 16, wherein the phospholipid is selected from the group consisting of a cocadmidopropyl PG-dimonium chloride phosphate salt, a ricinoleamidopropyl PG-dimonium chloride phosphate, a dilinoleamidopropyl PG-dimonium chloride phosphate, sodium cocamidopropyl PG-dimonium chloride phosphate and sodium dilinoleamidopropyl PG-dimonium chloride phosphate, a dimer dilinoleamido-propyl PG-dimonium chloride phosphate; linoleamidopropyl PG-dimonium chloride phosphate dilinoleamidopropyl PG-dimonium chloride phosphate, a 1-propanaminium, 3,3',3''-[phosphinylidynetris(oxy)]tris[N-(3-aminopropyl)-2-hydroxy-N,N-dimethyl-, N,N',N'''-tri-C$_{6-18}$ acyl derivative trichlorides, at least one fatty acid amidopropyl propylene glycol dimonium phosphate salt wherein the fatty acid is a C$_{10}$ C$_{25}$ fatty acid and mixtures thereof.

19. A method of stimulating a subterranean formation penetrated by a well comprising contacting the formation with an acidizing composition comprising, as a first member, an inorganic or organic acid and, as a second member (a) an organophosphorus surfactant selected from the group consisting of amino phosphonates and phosphino carboxylates and the combination of urea or a urea derivative and a bifunctional organic compound comprising (i) at least one quaternary ammonium moiety and at least one —OH group; and further comprising at least one of the following:

(a) retarding spending of the acid by adsorbing the organophosphorus surfactant onto a surface of the formation; or (b) delaying spending of the inorganic or organic acid by limiting bonding sites for the acid with the organophosphorus surfactant adsorbed on a surface of the formation;

(c) enhancing the creation and penetration of wormholes by retarding or slowing down the spending of the acid wherein the formation is a carbonate formation;

(d) delaying spending of the acid with the second member, wherein the second member comprises the combination of urea or a urea derivative and a bifunctional organic compound comprising (i) at least one quaternary ammonium moiety and at least one —OH group; and (e) retarding spending of the acid in the formation by disrupting hydrogen bonding of water, limiting the rate of disassociation of the acid and decreasing transfer of an acid proton onto the surface of the formation.

\* \* \* \* \*